United States Patent [19]

Henrick

[11] 4,448,965
[45] May 15, 1984

[54] SUBSTITUTED CYCLOALKANEDIONES

[75] Inventor: Clive A. Henrick, Palo Alto, Calif.

[73] Assignee: Zoecon Corporation, Palo Alto, Calif.

[21] Appl. No.: 408,291

[22] Filed: Aug. 16, 1982

[51] Int. Cl.³ ............... C07D 213/64; C07D 213/74; A01N 43/40

[52] U.S. Cl. .................................. 546/302; 546/288; 546/296; 546/297; 546/300; 546/304; 546/307; 546/312; 260/465 D; 564/433; 564/434; 544/354; 548/221; 548/222; 548/329

[58] Field of Search ............... 546/288, 296, 297, 300, 546/302, 304, 307, 312

[56] References Cited

U.S. PATENT DOCUMENTS 4,133,675 0/1979 Schurter et al. ...................... 71/94
4,216,007 0/1980 Nishiyama et al. ................... 71/94
4,348,221 0/1982 Szczepanski et al. ................ 71/94

FOREIGN PATENT DOCUMENTS 4684281 of 1981 Japan.
WO81/00563 of 1981 PCT Int'l Appl.
2040923 of 1980 United Kingdom.

OTHER PUBLICATIONS

Lee, Chem. Abstracts, vol. 97, No. 15, Abst. No. 127,249, Oct. 11, 1982.

*Primary Examiner*—Alan L. Rotman
*Attorney, Agent, or Firm*—Jacqueline S. Larson; Donald W. Erickson

[57] ABSTRACT

Novel substituted cycloalkanediones and their use for the control of weeds.

5 Claims, No Drawings

SUBSTITUTED CYCLOALKANEDIONES

This invention relates to substituted cycloalkanediones and the use of these compounds for the control of weeds.

More particularly, the compounds of the present invention are represented by the following formula (A):

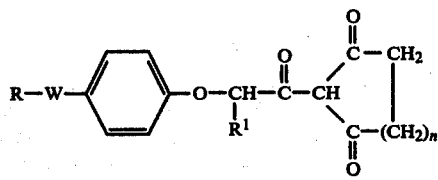

wherein,
n is zero, one, two or three;
R is

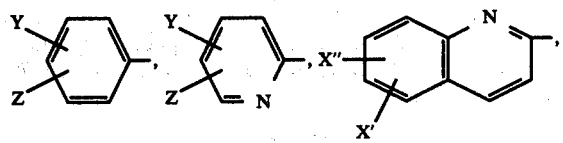

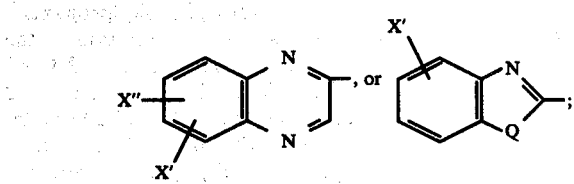

$R^1$ is hydrogen or lower alkyl;
W is oxygen, sulfur or amino;
Q is oxygen, sulfur or amino;
each of Y and Z is independently selected from hydrogen, lower alkyl, lower haloalkyl, lower alkoxy, lower haloalkoxy, halogen, nitro and cyano; and
Each of X' and X" is independently selected from hydrogen, lower haloalkyl, lower alkoxy, halogen and nitro, provided that both X' and X" cannot be trifluoromethyl, methoxy or nitro.

In the description and claims hereinafter, each of R, $R^1$, Q, W, X', X", and Y is as defined above, unless otherwise specified.

Compounds of the present invention of formula (A) can be synthesized by reacting an acid halide (I) (XX is Br, Cl or F) with an metal salt of a cycloalkanedione (II) in a non-polar organic solvent such as ether or tetrahydrofuran. The metal is preferrably chosen from lithium, thallium or magnesium. When the thallium salt is used, the halo atom (XX) should be fluoro.

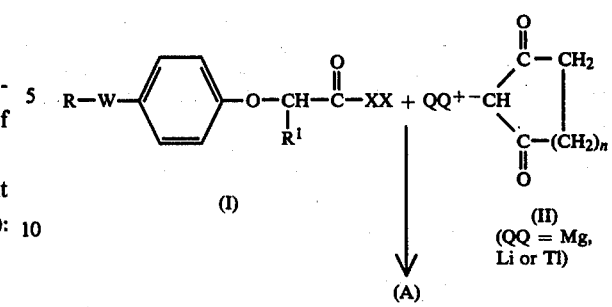

Alternatively, the compounds of formula (A) can be prepared by reacting together a carboxylic acid (III) and a cycloalkanedione (IV) in the presence of diethyl phosphorocyanidate and a base such as triethylamine or potassium carbonate.

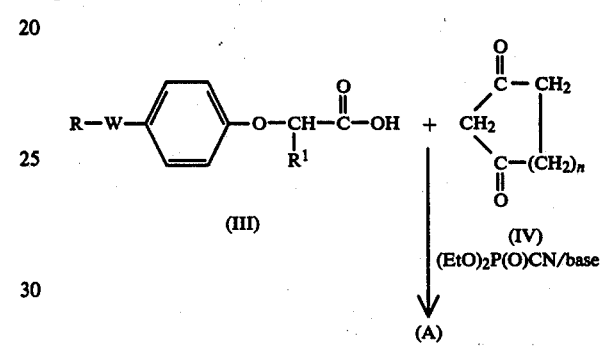

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "lower alkoxy" refers to an alkoxy group, straight or branched, having a chain length of one to eight carbon atoms. The term "lower haloalkoxy" refers to a lower alkoxy group substituted with one to three halogen atoms.

The compounds of the present invention have one or more asymmetric carbon atoms. The present invention includes each of the optically active isomers and racemic mixtures thereof. In the examples hereinafter, unless otherwise specified, the compound prepared is a racemic mixture.

The novel compounds of formula (A) are useful for the control of weeds, using pre- and/or post-emergent treatments. The compound can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half or less to ten pounds per acre.

While some of the compounds of the present invention have activity on broad leaf plants, the compounds, in general, demonstrate a higher level of herbicidal activity on the grass weeds. Grass plant (weed) species on which the compounds of the present invention show effective herbicidal activity include shattercane, crabgrass, sprangletop, wild oats, bermudagrass, tall fescue, rice, wheat, barley, corn, blue panicum, foxtails, rough bluegrass, winter rye, annual ryegrass, watergrass and Johnsongrass. It appears to be most effective to apply the active compound prior to the heading stage of the grass weed.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The optimum usage of a compound of the present invention is readily determinable by one of ordinary skill in the art using routine testing such as greenhouse testing and small plot testing.

The compounds of the present invention, in view of their broadspectrum grass weed herbicidal activity, can be advantageously combined with broadleaf weed herbicides for broadspectrum postemergence weed control in most broadleaf crops. Examples of herbicides which can be combined with a compound of the present invention include glyphosate, bentazone, diuron, paraquat, 2,4-D, 2,4-DB, diquat, endothal, dinoseb, dicamba, norflurazon, nitrofen, cyanozine, methazole, mefluidide, metribuzin, cycloate, fluometuron, linuron, dalapon, bifenox, and alachlor for controlling a broad spectrum of weeds.

The term "herbicide," as used herein, refers to an active ingredient which modifies the growth of plants because of phytotoxic or plant growth regulating properties so as to retard the growth of the plant or damage the plant sufficiently to kill it.

The following examples are provided to illustrate the practice of the present invention. Temperature is given in degrees Centigrade. "RT" means room temperature.

EXAMPLE 1

Ethyl bromide (6 g, 55 mmol) is added to magnesium turnings (1.34 g) in the presence of tetrahydrofuran (THF; 15 ml). After reaction is complete, the solution is diluted to 50 ml with THF cooled in an ice bath and cyclopentane-1,3-dione (50 mmol) is added rapidly with stirring. THF (250 ml) is added to this mixture and it is allowed to warm to RT. 2-[4-(4-Trifluoromethylphenoxy)phenoxy]propionic acid chloride (55 mmol) is added dropwise with stirring, and the mixture is allowed to stand at RT for 30 minutes. It is then poured into a mixture of ice, water and ether. The aqueous layer is extracted several times with ether. The combined ether extracts are washed with water, dried over sodium sulfate and the solvent is removed to give 2-[[2-[4-(4-trifluoromethylphenoxy)phenoxy]propionyl]]cyclopentane-1,3-dione (V; Y is H, Z is CF$_3$, R$^1$ is CH$_3$ and n is one).

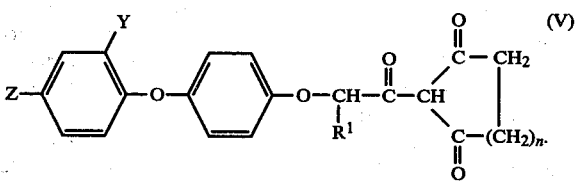

EXAMPLE 2

Following the procedure of Example 1, the magnesium salt of cyclopentane-1,3-dione is reacted with each of 2-[4-(2-chloro-4-trifluoromethylphenoxy)phenoxy]-propionic acid chloride, (2-[4-(2,4-diclorophenoxy)-phenoxy]propionic acid chloride and 2-[4-(2-nitro-4-trifluoromethylphenoxy)phenoxy]propionic acid chloride to yield, respectively, 2-[[2-[4-(2-chloro-4-trifluoromethylphenoxy)phenoxy]propionyl]]cyclopentane-1,3-dione (V; Y is Cl, Z is CF$_3$, R$^1$ is CH$_3$ and n is one), 2-[[2-[4-(2,4-dichlorophenoxy)phenoxy)propionyl]-]cyclopentane-1,3-dione (V; each of Y and Z is chloro, R$^1$ is CH$_3$ and n is one), &

2-[[2-[4-(2-nitro-4-trifluoromethoxyphenoxy)phenoxy]propionyl]]cyclopentane-1,3-dione (V; Y is NO$_2$, Z is CF$_3$, R$^1$ is CH$_3$ and n is one).

EXAMPLE 3

To THF (250 ml) under N$_2$ with stirring is added cyclopentane-1,3-dione (0.10 mol) and 2,2'-bipyridyl (~3–5 mg) as an indicator. After cooling to −70°, n-butyllithium in hexane is added slowly while the temperature is allowed to rise to −5° near the end of the addition (~130 ml of 1.6 M solution, 0.20 mol). After the pink indicator persists at −5°, the mixture is re-cooled to −65° and 4-(4-trifluoromethylphenoxy)-phenoxyacetyl chloride is added dropwise over 5 min. After 1 hour, the reaction mixture is diluted with water and ether is added. The organic layer is washed with water, dried over sodium sulfate and concentrated in vacuo to give 2-[4-(4-trifluoromethylphenoxy)phenoxyacetyl]cyclopentane-1,3-dione (V; Y is H, Z is CF$_3$, R$^1$ is H and n is one).

EXAMPLE 4

2-[4-(4-Trifluoromethylphenoxy)phenoxy]propionic acid fluoride (0.10 mol) is added to a solution of the thallium salt of cyclohexane-1,3-dione in ether (200 ml) over a period of 30 minutes. The mixture is filtered and the filtrate is concentrated to give 2-[[2-[4-(4-trifluoromethylphenoxy)phenoxy]propionyl]]cyclohexane-1,3-dione (V; Y is H, Z is CF$_3$, R$^1$ is CH$_3$ and n is two).

In the same manner, 2-[[2-[4-(4-trifluoromethylphenoxy)phenoxy]propionic acid fluoride is reacted with the thallium salt of cyclobutane-1,3-dione to yield 2-[[2-[4-(4-trifluoromethylphenoxy)phenoxy]propionyl]]cyclobutane-1,3-dione (V; Y is H, Z is CF$_3$, R$^1$ is CH$_3$ and n is zero).

The thallium salts of cyclohexane-1,3-dione and of cyclobutane-1,3-dione can be prepared as described by J. M. McIntosh et al., Can. J. Chem. 51:843 at 846 (1973), the disclosure of which is incorporated herein by reference.

EXAMPLE 5

Following the procedure of Example 3, the lithium salt of cyclopentane-1,3-dione is reacted with each of the acid chlorides under column I to give the corresponding cyclopentanedione under column II.

I 1. 2-[4-(3-chloro-5-trifluoromethyl-2-pyridyloxy)-phenoxy]propionic acid chloride
2. 2-[4-(5-trifluoromethyl-2-pyridyloxy)phenoxy]propionic acid chloride
3. 2-[4-(6-fluoro-2-quinolyloxy)phenoxy]propionic acid chloride
4. 2-[4-(6-chloro-2-quinoxalinyloxy)phenoxy]propionic acid chloride 5. 2-[4-(benzo-1,3-oxazolyl-2-oxy)phenoxy]propionic acid chloride

II 1. 2-[[-2-[4-(3-chloro-5-trifluoromethyl-2-pyridyloxy)-phenoxy]propionyl]]cyclopentane-1,3-dione
2. 2-[[2-[4-(5-trifluoromethyl-2-pyridyloxy)phenoxy]-propionyl]]cyclopentane-1,3-dione
3. 2-[[2-[4-(6-fluoro-2-quinolyloxy)phenoxy]propionyl]]cyclopentane-1,3-dione
4. 2-[[-2-[4-(6-chloro-2-quinoxalinyloxy)phenoxy]propionyl]]cyclopentane-1,3-dione
5. 2-[[2-[4-(benzo-1,3-oxazolyl-2-oxy)phenoxy]propionyl]]cyclopentane-1,3-dione

What is claimed is:

1. A compound of the following formula (A):

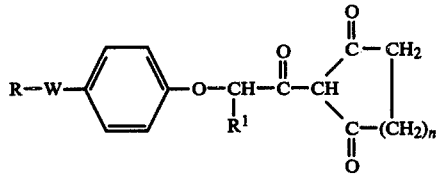

wherein,
n is zero, one, two or three;
R is

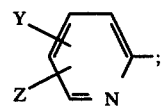

$R^1$ is hydrogen or lower alkyl;
W is oxygen, sulfur or amino; and
each of Y and Z is independently selected from hydrogen, lower haloalkyl and halogen.

2. A compound according to claim 1 wherein Y is hydrogen and Z is trifluoromethyl.

3. A compound of the following formula, according to claim 1:

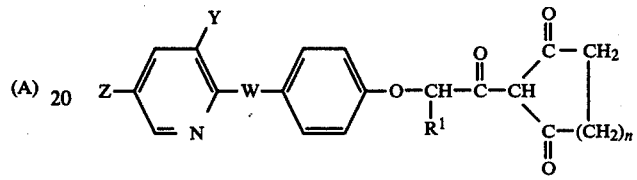

4. A compound according to claim 3 wherein W is oxygen, $R^1$ is methyl, n is one or two, Y is hydrogen chloro and Z is chloro or trifluoromethyl.

5. A compound according to claim 4 wherein Y is chloro and Z is trifluoromethyl.

* * * * *